(12) United States Patent
Parmley (10) Patent No.: US 11,335,445 B2
(45) Date of Patent: May 17, 2022

(54) METHOD, APPARATUS, AND SYSTEM TO MANAGE PATIENT TREATMENT

(71) Applicant: KONICA MINOLTA BUSINESS SOLUTIONS U.S.A., INC., San Mateo, CA (US)

(72) Inventor: John Parmley, Foster City, CA (US)

(73) Assignee: KONICA MINOLTA BUSINESS SOLUTIONS U.S.A., INC., San Mateo, CA (US)

(*) Notice: Subject to any disclaimer, the term of this patent is extended or adjusted under 35 U.S.C. 154(b) by 0 days.

(21) Appl. No.: 16/837,967

(22) Filed: Apr. 1, 2020

(65) Prior Publication Data
US 2021/0313030 A1    Oct. 7, 2021

(51) Int. Cl.
*G16H 20/00* (2018.01)
*G16H 20/10* (2018.01)
*G16H 50/30* (2018.01)
*G16H 20/60* (2018.01)
*G16H 20/30* (2018.01)

(52) U.S. Cl.
CPC .............. *G16H 20/10* (2018.01); *G16H 20/30* (2018.01); *G16H 20/60* (2018.01); *G16H 50/30* (2018.01)

(58) Field of Classification Search
CPC .......................... G06Q 50/22–24; G16H 20/10
See application file for complete search history.

(56) References Cited

U.S. PATENT DOCUMENTS

| 5,933,136 A | * | 8/1999 | Brown ............... H04N 7/17345 715/741 |
| 8,224,667 B1 | * | 7/2012 | Miller .................... G16H 20/10 705/2 |
| 2004/0193446 A1 | * | 9/2004 | Mayer .................... G16H 20/10 705/2 |
| 2007/0033072 A1 | | 2/2007 | Bildirici |
| 2008/0077436 A1 | | 3/2008 | Muradia |
| 2009/0043633 A1 | * | 2/2009 | Nadas .................... G06Q 50/00 705/7.15 |

(Continued)

FOREIGN PATENT DOCUMENTS

| KR | 10-2017-0057569 | 5/2017 | |
| WO | WO-2008057606 A2 * | 5/2008 | ............. G16H 20/10 |

OTHER PUBLICATIONS

Medication Adherence for Physicians; RheumInfo; Captured by the Internet Archive on Jun. 9, 2015 (Year: 2015).*

*Primary Examiner* — John A Pauls
(74) *Attorney, Agent, or Firm* — Squire Patton Boggs (US) LLP (57) ABSTRACT

A care plan risk rating ($CPR^2$) system and method enables physicians and other clinicians to manage patient health care plans remotely in response to patient input to generate $CPR^2$ values. In one aspect, patients under care for a particular condition respond to a series of questions related to that condition. The questions may be weighted according to predetermined criteria which a physician or clinician may set. Based on the $CPR^2$ values, the physician or clinician may alter a care plan for a patient or a group of patients. In one aspect, patients with $CPR^2$ values in a predetermined range may be grouped into a cohort, and their care plans managed as a group.

6 Claims, 4 Drawing Sheets

(56) References Cited

U.S. PATENT DOCUMENTS

2012/0310700 A1* 12/2012 Kurtz ............... G06Q 40/08
                                                      705/7.28
2013/0096953 A1*  4/2013 Beverly ............ G16H 20/10
                                                      705/3
2018/0113985 A1*  4/2018 Gandy ............. G16H 40/63

* cited by examiner

METHOD, APPARATUS, AND SYSTEM TO MANAGE PATIENT TREATMENT

BACKGROUND OF THE INVENTION

Aspects of the present invention relate to facilitating of patient treatment, and more particularly, to the formulation, monitoring, and modification of patient treatment plans.

Physicians and other clinicians give patients instructions that describe what the patient should do, and when and where to do it. The instructions can include, but are not limited to taking prescriptions, following a certain diet, performing certain physical activity, attending physical therapy, completing imaging (X-ray, computed tomography (CT), magnetic resonance imaging (MRI), Ultrasound, etc.) tests, or getting other lab tests and procedures done. All of these instructions fall under an umbrella which may be termed a care plan.

Research has shown that patients who do not follow a care plan are more likely to have poorer clinical outcomes than patients who do follow a care plan. Poorer clinical outcomes can require additional medical attention and treatment, at increased long-term cost.

To address patient lack of compliance, physicians and clinicians have tried various manual and technology driven methods which have had limited success at best. These approaches have included anything from phone calls, to visits, to Internet of Things (IoT) applications, all designed to find out if patients are taking their prescriptions, eating properly, exercising, getting physical therapy, getting tests done, getting to physician/clinician appointments, etc. Each of these patient compliance monitoring methods employs what amounts to a siloed approach.

It would be desirable for a physician/clinician to be able to acquire data on patient compliance without having to aggregate data from all of the various silos.

It also would be desirable for a physician/clinician to be able to take advantage of massed data on patient compliance regarding care plans designed to treat particular conditions, to devise improved care plans, without having to aggregate data from all of the various silos.

SUMMARY OF THE INVENTION

To address the above-described and other issues, aspects of the present invention relate to what is termed a Care Plan Risk Rating ($CPR^2$) Score. As will be described, $CPR^2$ avoids the need for labor-intensive aggregation of siloed data, and enables a physician/clinician to obtain a quick assessment for decision making when it comes to patient treatment and care. In one aspect, by having $CPR^2$ scores for multiple patients under treatment for a similar condition (e.g. diabetes), $CPR^2$ can improve treatment outcome through improved monitoring of patient compliance and coordination of care plan modifications individually or in bulk to account for results that patients report. A physician's/clinician's ability to understand which patients are more compliant, or less compliant, with a care plan can yield indices and insights to facilitate actions to improve patient compliance with and adherence to the care plan.

Aspects of $CPR^2$ rely on patient reported data. By comparing a patient's care plan and the collected patient reported data, it is possible to obtain an index or rating signifying a level of the patient's compliance/adherence. The higher the rating, the higher the level of compliance/adherence. In one aspect, health care providers can weight each category of a care plan based on requirements of individual patients or of a group of patients (for example, patients who share a particular health-related issue, such as diabetes). By knowing the $CPR^2$ for each patient in a group of patients, a provider can then create cohorts of patients that meet specific $CPR^2$ criteria so that the provider can take future action to improve the $CPR^2$ for individuals and groups of patients.

The $CPR^2$ score gives physicians and clinicians insights into patients who are not compliant/adherent. For example, in an office setting, many physicians or clinicians only get a chance to assess a patient's progress during visits, and do not have access or opportunity to determine whether a prescribed care plan is working while a patient is at home. Similarly, even though physicians and clinicians in a hospital setting may have the benefit of numerous care/case managers to follow up on patients and provide feedback through existing systems, the follow-up process is inconsistent. Analyzing the results of follow-up and deciding how to proceed can entail reading through numerous assessments, and consequently can be very time consuming.

Looking at the $CPR^2$ scores for groups of patients, not just for a particular physician or clinician but also for groups of physicians or clinicians employing identical or similar care plans, can help physicians and clinicians both examine data for identical or very similar care plans, but also compare and contrast data for care plans being used for the same patient condition. One effect of this wide scale use of data is to provide physicians and clinicians with additional insights and enhanced decision making abilities by enabling access to a much greater amount of data.

BRIEF DESCRIPTION OF THE DRAWINGS

Aspects and embodiments of the present invention now will be described in detail with reference to the accompanying drawings, in which.

DETAILED DESCRIPTION

In the following description, for ease of reference a physician or a clinician may be referred to as one or the other. Such reference should be understood as being applicable to either. Also in this description, unless called out otherwise, a "provider" will refer to a larger organization that may employ a plurality of physicians and/or clinicians.

In one aspect, determining a $CPR^2$ value starts with patient data. In an embodiment, a patient may enter data into an app (for example, on a mobile device such as a smartphone or tablet), or into a desktop or notebook computer (for example, via a Web-based portal). The data that the patient enters may be responsive to questions relating to the patient's care plan. The questions may fall into a number of categories, including but not limited to prescriptions, other medication, nutritional supplements, diet, exercise, physical therapy, office visits, imaging, laboratory work, and the like. This list is not intended to be exhaustive, but rather is intended to be illustrative. Ordinarily skilled artisans will recognize that there may be other aspects of a patient's care plan that may be relevant to ask about.

In an embodiment, care plan data may come from various sources besides the patient. For example, Electronic Medical Records (EMR) and Electronic Health Records (EHR) may have relevant data. Other types of provider-based systems, including but not limited to Population Health/Analytic platforms, Care Management systems, or Case Management systems, also could be sources of relevant data.

Care plans and care plan data may be stored centrally, at a server or in a cloud-based network. The plans and the data may be patient-specific, or may apply to a group, as will be discussed herein. Patient identifiers that may be used to access the data may include such items as name, address, Social Security number (SSN), Medical Record Number, Master Patient Index, or other identifiers which ordinarily skilled artisans will recognize.

The app or portal may register and validate the patient to verify the patient's circumstance, and identify the proper questions for the patient's care plan. There may be a list of care plan-related questions to which the patient can respond. By answering the questions, the patient may self-report his/her compliance with the care plan. In an embodiment, the patient's responses may be stored locally, but such local storage is not required. The patient's responses may be transmitted to a central system, which in an embodiment, may be in a server, or in the cloud.

For a particular condition, the questions may allow a patient to provide discrete data which the system can collect in a structured fashion. The data may be in the form of yes or no responses, or may be in the form of numerical responses, or may be responses to multiple-choice questions.

Figure 1:
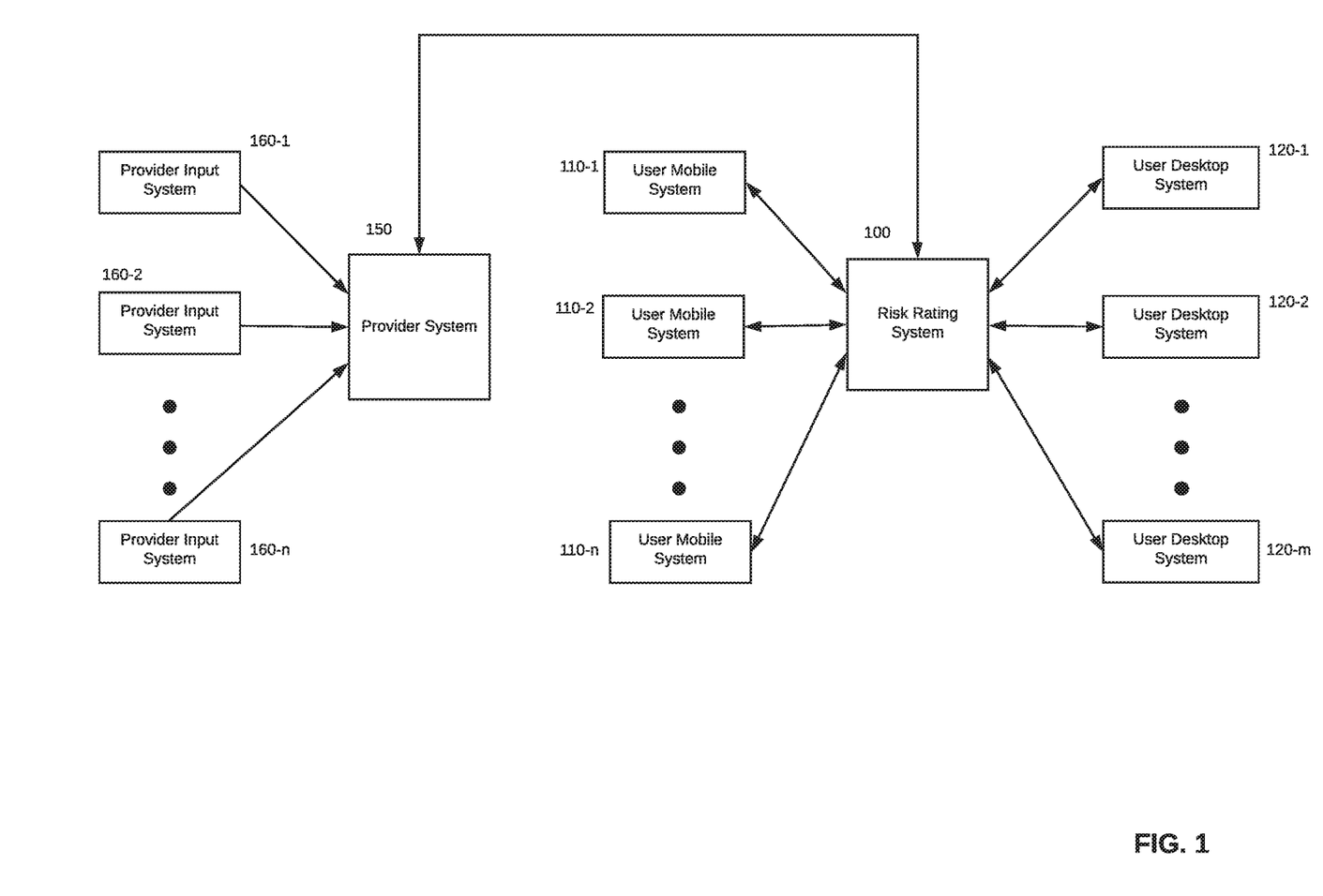
FIG. 1 is a high level block diagram of a system to generate and compile $CPR^2$ values.

Looking at FIG. 1, a system includes a risk rating system 100 and a provider system 150. In an embodiment, the systems 100, 150 may be physically separate, but in other embodiments, the systems 100, 150 may be physically connected to each other, or even integral one with the other. In one aspect, the risk rating system 100 communicates with one or more user mobile systems 110-1, . . . 110-$n$ (e.g. smartphone, tablet) and one or more desktop systems 120-1, . . . 120-$n$ (e.g. desktop, notebook computer). A user may log in via one of the mobile or desktop systems and may complete the questionnaire. The provider system 150 may communicate with the risk rating system 100 to provide data regarding the care plan, and to receive $CPR^2$ calculations from the risk rating system 100. Physicians/clinicians may access the provider system 150 via one or more provider input systems 160-1, . . . , 160-$n$.

In an embodiment, physicians and clinicians may access provider system 150 to review $CPR^2$ values for patients or groups of patients, in lieu of reviewing individual questions and answers. As will be discussed below, a physician may provide the questions, and may assign weights to the questions, according to the importance or significance the physician ascribes to the answers in the overall care plan. By formulating the questions and assigning weights to the responses, the physician can rely on the patient's $CPR^2$ value to ascertain the extent of patient compliance, and to determine whether a care plan needs to be altered. In an embodiment, a physician who is responsible for a number of patients who are being treated for the same condition can review the $CPR^2$ values for all of the patients, and may discern from that larger body of data the extent of the effectiveness of the care plan. For example, uniformly high $CPR^2$ values may indicate a care plan that patients are following. Depending on the extent of improvement of a patient's condition as a result of following such a care plan, a physician can determine whether to keep the plan as is, or whether to change it.

Similarly, uniformly low $CPR^2$ values may indicate a care plan that patients are not following as well. Depending on whether patients are improving as a result of following (or in this case, not following) such a care plan, the physician can determine whether to change the plan. For example, depending on the weights that the physician assigns to patient responses to particular questions or categories of questions, the physician may determine that diet or exercise regimens may be difficult for patients to comply with. The physician can decide whether to counsel a patient further, or to change one or both of the diet or exercise regimen, to improve patient compliance, as a higher resulting $CPR^2$ value would reflect.

Figure 2:
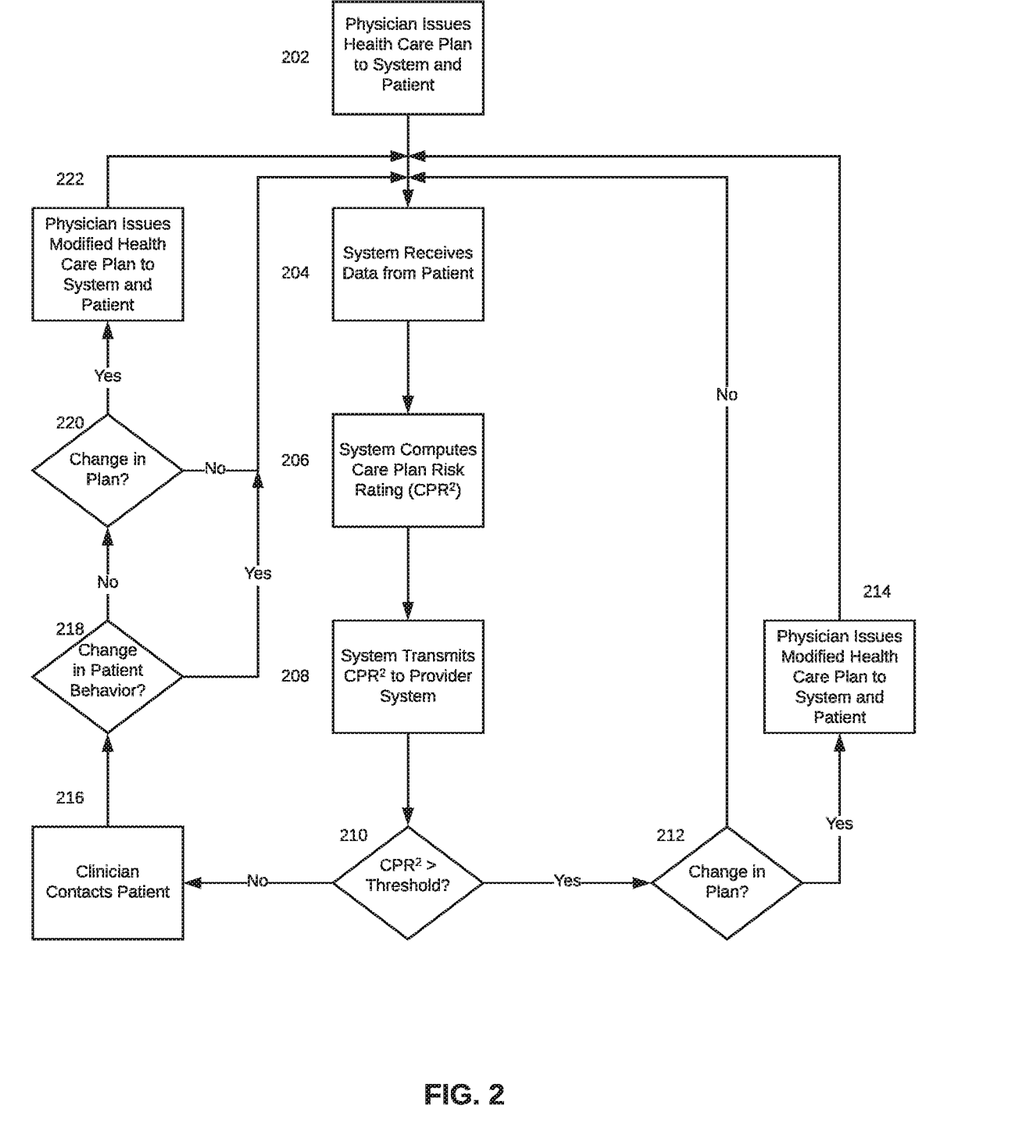
FIG. 2 is a high level flow chart for the generation and compilation of $CPR^2$ values, including the alteration of a care plan for an individual patient.

Looking at the flow of care plan implementation and modification more closely, in FIG. 2, at 202 a physician/clinician may develop a care plan, and may provide that plan to a patient, and to a system such as the system in FIG. 1. In developing a care plan, the physician/clinician may determine that some aspects of the plan are more important than others in terms of maintaining or improving a patient's condition. In one aspect, administration of the care plan may involve a patient's self-reporting of compliance with the various aspects of the plan. At 204, a patient provides that self-reporting to the risk rating system. At 206, the risk rating system takes the self-reported data and computes a $CPR^2$ value. At 208, the risk rating system transmits that $CPR^2$ value to the provider system, or may store the value for the physician's future retrieval and review.

At 210, if the $CPR^2$ value is above a predetermined threshold, indicating satisfactory compliance with the care plan, at 212 the physician can determine whether some change in the care plan might be appropriate. For example, if a diet and/or exercise regimen has been relatively rigorous and has had good effect, a physician may decide to instruct a less rigorous diet and/or exercise regimen. As another example, if a patient is taking his/her prescribed medication (leading to a higher $CPR^2$ value) but does not show improvement, a physician may decide to change the medication and/or the dosage. If a change is appropriate, then at 214 the physician modifies the care plan and sends the modified plan to the patient. When the patient next logs in to complete the list of questions, the patient will provide data on compliance with that modified plan. If a change is not appropriate, then the patient continues to provide data on compliance with the unmodified plan.

At 210, if the $CPR^2$ value is not above the predetermined threshold, at 216 a physician or someone associated with the physician may contact the patient to determine a reason or reasons for noncompliance, and in one aspect, may encourage compliance. Contact with the patient may be via electronic means (phone, email, text, or an app) or via a personal visit (the patient may come to the physician, or may receive a visit from treatment staff), or even via mail (e.g. a letter or form letter). At 218, there is a determination whether there is a change in patient behavior as a result of the contact. If there is, flow returns to 204, and the risk rating system continues to receive data from the patient. If there is no change in patient behavior, flow will go to 220. In one aspect, there may be an analysis of why the behavior did not change. For example, if the behavior did not change simply because the patient is non-compliant or not sufficiently compliant, it may be determined that the situation should continue to be monitored, without changing the treatment plan. In that event, flow would return to 204, and the risk rating system would continue to receive data from the patient.

In one aspect, based on an outcome of contact with the patient, it may be determined that patent behavior did not change because the patient regimen is too demanding. Alternatively, the physician may review the patient's data and conclude that a different approach may be helpful. Either circumstance would lead to a change in the patient's treatment plan, with a modified plan going to the patient at 222, and patient monitoring with the modified plan in place would occur.

In another aspect, $CPR^2$ values for multiple patients being treated for a particular condition may be considered together, in what may be termed a cohort. A cohort may comprise all or some of the patients of a particular physician or clinician, or of a group of physicians or clinicians at a particular provider. It is within the contemplation of aspects of the invention to have a cohort comprise all or some of the patients of physicians or clinicians at multiple providers, where care plans are being contemplated and/or analyzed on a larger scale.

Figure 3:
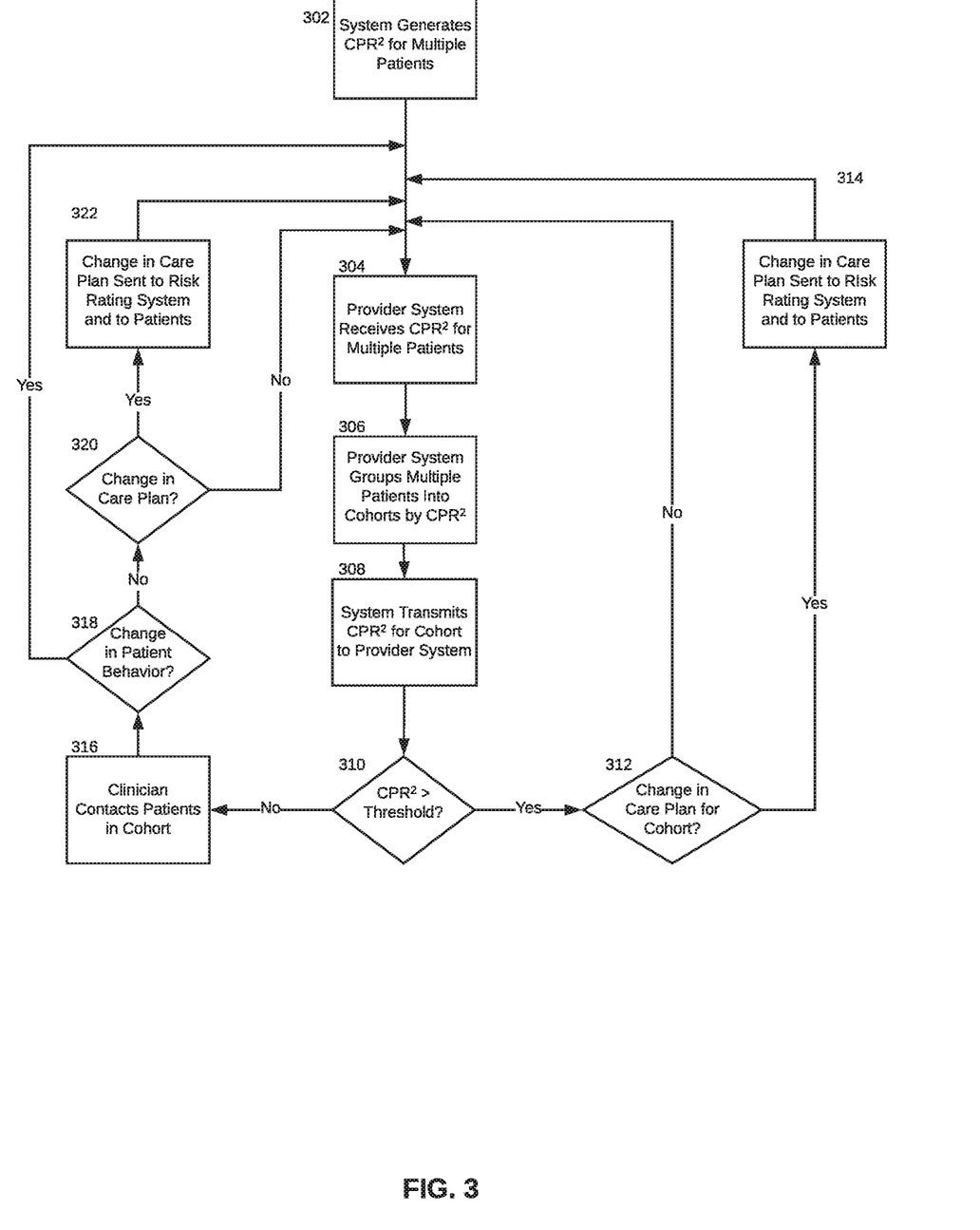
FIG. 3 is a high level flow chart for the generation and compilation of $CPR^2$ values, including the alteration of a care plan or plans for groups of patients under treatment for a particular condition.

Looking at FIG. 3, at 302 the risk rating system may generate $CPR^2$ values for multiple patients with similar care plans. In an embodiment, at 304, a provider system may receive those values, and a physician or other clinician may review them. At 306, the physician may use those values to instruct the provider system to group his/her patients into a cohort according to $CPR^2$. In another embodiment, at 306, the risk rating system may use those values to group patients into one or more cohorts, for a particular physician, or for multiple physicians within a provider, or even across multiple providers. A cohort may comprise patients with the same or similar care plans, or with one or more similar aspects to their care plans. In one aspect, as just alluded to, a cohort may reflect a predetermined degree of compliance with similar care plans, for example, $CPR^2$ values above a predetermined threshold, or between predetermined values, or below a predetermined threshold. Different cohorts thereby may reflect different degrees of compliance with similar care plans. Physicians can look at particular cohorts, ascertain the progress being made in addressing the conditions of patients within the cohort, and thereby may determine whether a particular care plan is addressing patient needs. For example, looking at weights that physicians may assign to particular aspects of a care plan, a cohort may comprise patients with sufficiently similar portions or proportions of their care plans.

At 308, the risk rating system takes collective $CPR^2$ values for the cohorts and sends them to the provider system for a physician (or physicians, depending on the cohort composition) to review. At 310, a determination is made whether the $CPR^2$ value for the cohort is above a predetermined threshold. If so, then similarly to the discussion for FIG. 2, at 312 the physician(s) can determine whether some change in the care plan might be appropriate. For example, if a diet and/or exercise regimen has been relatively rigorous and has had good effect, the physician(s) may decide to instruct a less rigorous diet and/or exercise regimen. As another example, if patients in the cohort are taking their prescribed medication (leading to a higher $CPR^2$ value) but do not show improvement, the physician(s) may decide to change the medication and/or the dosage. If a change is appropriate, then at 314 the care plan is modified and then sent to the risk rating system and thence to the patients, and flow returns to 304. When the patients next log in to complete the list of questions, the patients will provide data on compliance to that modified plan. Based on input from all of the patients in the existing cohort, $CPR^2$ scores may change individually or overall. Depending on the changes, a different regrouping of patients into cohorts may be warranted. If a change is not appropriate, then flow still returns to 304, and the patients continue to provide data on compliance with the unmodified plan.

Turning back to 310, if the cohort $CPR^2$ value does not meet a predetermined threshold, at 316 the clinician(s) may contact patents in the cohort, to try to get better compliance. If at 318 it is determined that there is a change in patient behavior, then flow may return to 304 to look again at individual patient $CPR^2$ values. If there is no change or insufficient change in patient behavior, then at 320 a determination may be made whether there should be a change in the care plan, for reasons similar to those discussed with respect to FIG. 2. If there is no change in the care plan, flow may return to 304, and the patients continue to provide data on compliance with the unmodified plan. If there is to be a change in the care plan, then that occurs at 322, and patients will provide data on compliance with that modified plan.

Figure 4:
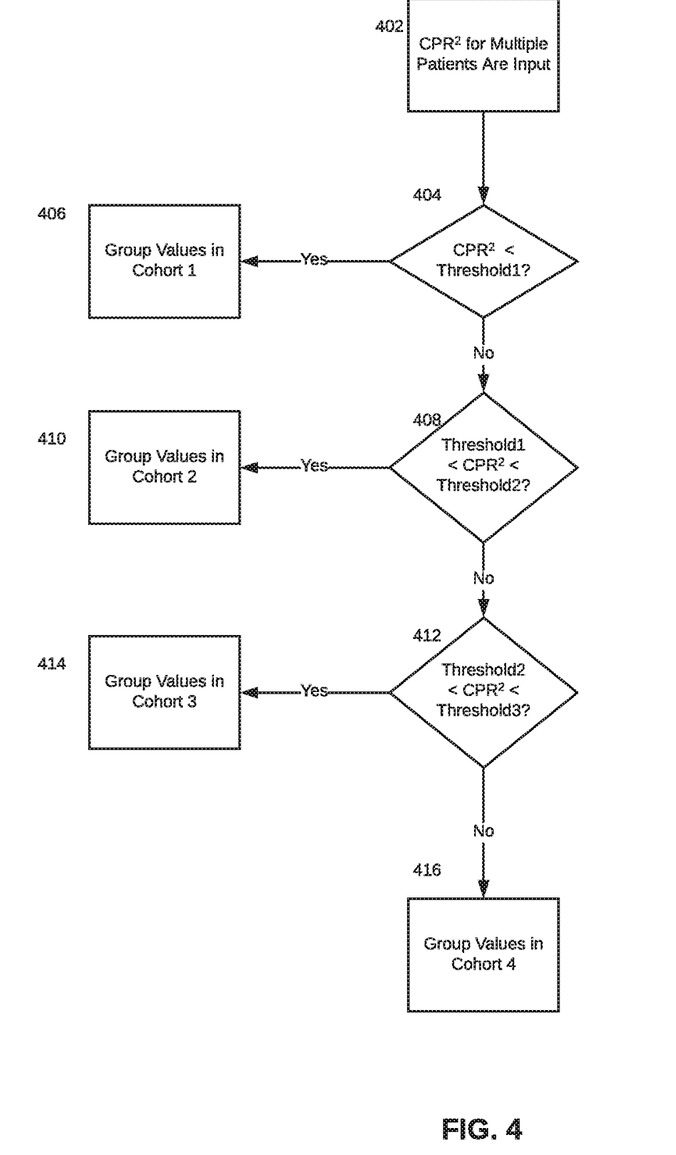
FIG. 4 is a high level flow chart describing an aspect of FIG. 3.

FIG. 4 shows additional detail for grouping of patients into cohorts. At 402, $CPR^2$ values for multiple patients are input. At 404, patient $CPR^2$ values exceeding a first threshold (Threshold1) are grouped into a cohort at 406. The remaining $CPR^2$ values are checked at 408. Those values that are between Threshold1 and a second threshold (Threshold2) are grouped into a second cohort at 410. The remaining $CPR^2$ values are checked again at 412. Those values that are between Threshold2 and a third threshold (Threshold3) are grouped into a third cohort at 414. The now-remaining $CPR^2$ values will be grouped into a fourth cohort at 416. Those $CPR^2$ values will be at or above Threshold3.

For simplicity of description, FIG. 4 addresses $CPR^2$ values that fall within any of four ranges. In different embodiments, there may be a greater number of thresholds, or a lower number of thresholds, in which case there will be a different number of ranges, and hence a different number of cohorts. The number of cohorts that may be most helpful or useful in a particular situation can depend on a number of criteria, including but not limited to the condition being treated, the criteria addressed in the questions to patients, and/or the focus of a particular physician or group of physicians.

Ordinarily skilled artisans will appreciate that, particularly for large groups of patients and correspondingly large amounts of data, computer processing in some fashion will be indispensable to carrying out aspects of the invention. Even if an individual, or even a group of individuals, might be able to handle or process such large quantities of data, the time that it would take to do so would be prohibitive, such that the results would be useless. In the intervening long period of time, patients may no longer be treated; one or more care plans may need to be altered but cannot be because individuals are processing the data and are taking an excessively long time to do so; or one or more patients may better be grouped in a different cohort. Ordinarily skilled artisans will appreciate other consequences of changes in $CPR^2$ values for one or more patients in a cohort.

In an embodiment, a patient may log in to the risk rating system daily, or weekly, or monthly to provide responses. The risk rating system questions to the patient may reflect daily responses, or weekly responses, or monthly responses. Question examples may relate to some or all of the following, among others:

1) Prescriptions:
   a. Have you had all your prescriptions filled at the pharmacy? 1=none, 10=all
   b. How many of your prescriptions have you had filled? 1=none, 10=all
2) Medication:
   a. Did you take all of your medications today/this week/this month? 1=none, 10=all
   b. Did you take all of your medications at the correct times today/this week/this month? 1=none, 10=all
   c. Did you take all of your medications in the correct dosages today/this week/this month? 1=none, 10=all
   d. How many of your medications did you take today/this week/this month?
   e. How many of your medications did you take at the correct times today/this week/this month?
   f. How many of your medications did you take in the correct dosages today/this week/this month?
3) Nutritional Supplements:
   a. Did you take all of your supplements today/this week/this month? 1=none, 10=all
   b. Did you take all of your supplements at the correct times today/this week/this month? 1=none, 10=all
   c. Did you take all of your supplements in the correct dosages today/this week/this month? 1=none, 10=all
   d. How many of your supplements did you take today/this week/this month?
   e. How many of your supplements did you take at the correct times today/this week/this month?
   f. How many of your supplements did you take in the correct dosages today/this week/this month?
4) Diet:
   a. Have you limited your daily calorie intake to less than 2000 calories today/this week/this month? 3000 calories? 1=no, 10=yes
   b. How many times have you limited your daily calorie intake to less than 2000 calories this week/this month? 3000 calories?
   c. Have you limited your daily fat intake to less than X grams today/this week/this month? Y grams? 1=no, 10=yes
   d. How many times have you limited your daily fat intake to less than X grams this week/this month? Y grams?
   e. Have you consumed at least X grams of fiber today/this week/this month? Y grams? 1=no, 10=yes
   f. How many times have you consumed at least X grams of fiber this week/this month? Y grams?
5) Exercise:
   a. Did you walk at least 7000 steps today/each day this week/each day this month? 1=yes, 2=no
   b. How many times did you walk at least 7000 steps this week/this month?
6) Tests:
   a. Have you completed all medical imaging tests as prescribed? 1=yes, 2=no
   b. Have you completed all required lab tests as prescribed? 1=yes, 2=no
7) Other Procedures:
   a. Have you completed all other required procedures as prescribed? 1=yes, 2=no
8) Therapy:
   a. Did you complete the required physical therapy today/this week/this month? 1=yes, 2=no
   b. How many times did you go to physical therapy this week/this month?

Ordinarily skilled artisans will appreciate that, depending on the disease, disorder, or condition being treated, there may be more questions, or fewer questions. Individual physicians may select all or a few of the possible questions, depending on the care plan, and/or on the severity of a particular patient's condition.

A physician may assign a weight percentage to each question and accordingly to the patient response, such that the sum of all the percentages totals 100%. Along the lines outlined above, in an embodiment a physician may categorize questions into generic groups such as medication, diet, exercise, etc. so that there can be multiple different questions within a particular category. In this fashion, it is possible to report categories of questions separately and even independently. A physician or clinician can use aspects of the foregoing framework to create/enter the questions s/he feels are important in creating the care plan and the resulting $CPR^2$ rating. Aspects of the framework may employ patient responses and the accompanying question percentages to create the $CPR^2$ number.

An example of a generic format for questions and weightings might be as follows:

| Questions | Category | Weighted Percent |
| --- | --- | --- |
| Question 1 | Prescriptions | Percent Importance |
| Question 2 | Prescriptions | Percent Importance |
| Question 3 | Medication | Percent Importance |
| Question 4 | Medication | Percent Importance |
| Question 5 | Nutritional Supplements | Percent Importance |
| Question 6 | Diet | Percent Importance |
| Question 7 | Diet | Percent Importance |
| Question 8 | Exercise | Percent Importance |
| Question 9 | Tests | Percent Importance |
| Question 10 | Tests | Percent Importance |
| Question 11 | Procedures | Percent Importance |
| Question 12 | Therapy | Percent Importance |
| ... | ... | ... |
| Question n | Others | Percent Importance |
| | Sum | 100% |

This framework could be specific to the patient or a group of patients with similar care plans. The framework could be modified on demand to add/subtract or edit questions, categories or weighted percentages.

In an embodiment, the $CPR^2$ value may be calculated by multiplying the "Percent Importance"×Percent Completed.

| Questions | Category | Percent | Score from Patient | Category Score |
| --- | --- | --- | --- | --- |
| Question 1 | Prescriptions | Percent Importance | Patient Score | "=Percent × Patient Score" |
| Question 2 | Prescriptions | Percent Importance | Patient Score | "=Percent × Patient Score" |
| Question 3 | Medication | Percent Importance | Patient Score | "=Percent × Patient Score" |
| Question 4 | Medication | Percent Importance | Patient Score | "=Percent × Patient Score" |

| Questions | Category | Percent | Score from Patient | Category Score |
|---|---|---|---|---|
| Question 5 | Nutritional Supplements | Percent Importance | Patient Score | "=Percent × Patient Score" |
| Question 6 | Diet | Percent Importance | Patient Score | "=Percent × Patient Score" |
| Question 7 | Diet | Percent Importance | Patient Score | "=Percent × Patient Score" |
| Question 8 | Exercise | Percent Importance | Patient Score | "=Percent × Patient Score" |
| Question 9 | Tests | Percent Importance | Patient Score | "=Percent × Patient Score" |
| Question 10 | Tests | Percent Importance | Patient Score | "=Percent × Patient Score" |
| Question 11 | Procedures | Percent Importance | Patient Score | "=Percent × Patient Score" |
| Question 12 | Therapy | Percent Importance | Patient Score | "=Percent × Patient Score" |
| ... | ... | ... | ... | ... |
| Question n | Others | Percent Importance | Patient Score | "=Percent × Patient Score" |
| | Sum | 100% | | $CPR^2$ # |

The $CPR^2$ value may be calculated, and can be stored or forwarded to other clinical systems according to the physician's or clinician's, or the provider's preferences. An example of this calculation may be as follows:

| Questions | Category | Percent | Score from Patient | |
|---|---|---|---|---|
| Question 1 | Prescriptions | 10% | 8 | .8 |
| Question 2 | Prescriptions | 5% | 5 | .25 |
| Question 3 | Medication | 5% | 7 | .35 |
| Question 4 | Medication | 5% | 10 | .5 |
| Question 5 | Nutritional Supplements | 5% | 6 | .30 |
| Question 6 | Diet | 10% | 10 | 1.0 |
| Question 7 | Diet | 7% | 2 | .14 |
| Question 8 | Exercise | 10% | 8 | .8 |
| Question 9 | Tests | 12% | 10 | 1.2 |
| Question 10 | Tests | 10% | 6 | .6 |
| Question 11 | Procedures | 8% | 10 | .8 |
| Question 12 | Therapy | 8% | 10 | .8 |
| ... | ... | ... | ... | ... |
| Question n | Others | 5% | 5 | .25 |
| | Sum | 100% | | 7.89 |

In accordance with the description of FIGS. 3 and 4, $CPR^2$ values within a given range, for example, one of the ranges in FIG. 4, may cause patients to be grouped into a cohort. As an example, patients with $CPR^2$ values below 5.0 may be in a first cohort. Patients with $CPR^2$ values between 5 and 6 may be in a second cohort. Patients with $CPR^2$ values between 6 and 7 may be in a third cohort. Remaining patients, with $CPR^2$ values above 7, may be in a fourth cohort. The ranges of values and number of cohorts can vary as desired.

Ordinarily skilled artisans will appreciate the following regarding aspects of the present invention:

Physicians and clinicians and, where appropriate, providers, can adjust the framework for obtaining $CPR^2$ values based on individual or group requirements.

$CPR^2$ values can provide data on overall compliance with a care plan, as well as data on individual components of the care plan.

$CPR^2$ values may be provided independent of a particular physician or clinician, or even a particular provider. In a sense, the $CPR^2$ values may be said to be agnostic to physicians, clinicians, or providers.

In another sense, $CPR^2$ values may be considered to be agnostic to other technologies that providers use to obtain data, e.g. EMR/EHR, Population Health/Analytics Platforms, care management or case management systems, and the like.

While the foregoing describes embodiments according to aspects of the invention, the invention is not to be considered as limited to those embodiments or aspects. Ordinarily skilled artisans will appreciate variants of the invention within the scope and spirit of the appended claims.

What is claimed is:

1. A computer-implemented system to manage patient treatment through provision and selective alteration of patient care plans, the system comprising:
   a computer-implemented provider system to provide a care plan for each of a first plurality of patients in a first plurality of patient cohorts, said first plurality of patients being treated for a condition by physicians or clinicians at multiple health care providers;
   a computer-implemented risk rating system to communicate to each of the first plurality of patients, that patient's care plan, and to generate, for each of the first plurality of patients, responsive to:
   each patient's care plan and data pertaining to the patient; and
   medical and demographic data for all of the first plurality of patients,
   data for the patient and for all of the first plurality of patients coming from sources including Electronic Medical Records (EMR) and Electronic Health Records (EHR), Population Health/Analytic platforms, Care Management systems, and Case Management systems;
   a care plan risk rating, each care plan risk rating indicating a patient's degree of compliance with that patient's care plan, and calculated according to that patient's responses to a predetermined series of questions regarding that patient's care plan; and
   the provider system to store the responses and the care plan risk ratings;
   wherein, for a given condition for which the first plurality of patients is being treated, and responsive to a determination that one or more of the care plan risk ratings justifies a change in one or more of the care plans for the first plurality of patients, one of the risk rating system and the provider system communicates the change to those of the first plurality of patients whose care plan risk ratings justify the change, wherein the risk rating system collects the care plan risk ratings for the first plurality of patients and instructs the change responsive to the collective care plan risk ratings for the first plurality of patients;

wherein one of the provider system and the risk rating system assembles the care plan risk ratings for the first plurality of patients into a further plurality of patient cohorts, different from said first plurality of patient cohorts, according to predetermined criteria which comprise a predetermined threshold or a predetermined range for the assembled care plan risk ratings, wherein each of the further plurality of patient cohorts comprises care plan risk ratings for patients of a plurality of physicians, wherein a first one of the further plurality of patient cohorts comprises care plan risk ratings above a first threshold; a second one of the further plurality of patient cohorts comprises care plan risk ratings between the first threshold and a second threshold; and a third one of the further plurality of patient cohorts comprises care plan risk ratings above the second threshold, wherein care plan risk ratings above said second threshold indicate substantial compliance with care plans; and wherein one of the provider system and the risk rating system may implement said change in one or more of the care plans for the first plurality of patients in the third one of the further plurality of patient cohorts, responsive to the patients not showing sufficient improvement despite having care plan risk ratings above the second threshold.

2. A system as claimed in claim 1, wherein each of the predetermined series of questions has a weight assigned to it such that a sum of the weights for all of the predetermined series of questions equals 100%.

3. A system as claimed in claim 1, wherein the care plans comprise a plurality of items selected from the group consisting of prescriptions, medications, nutritional supplements, diet, exercise, laboratory tests, medical procedures, and one or more therapies.

4. A computer-implemented method of managing patient treatment through provision and selective alteration of patient care plans, the method comprising:

providing, via a computer-implemented provider system, a care plan for each of a first plurality of patients in a first plurality of patient cohorts, said first plurality of patients being treated for a condition by physicians or clinicians at multiple health care providers;

communicating, via a computer-implemented risk rating system, the care plans to each of the first plurality of patients;

generating, for each of the first plurality of patients, via the computer-implemented risk rating system, responsive to:

each patient's care plan and data pertaining to the patient; and medical and demographic data for all of the first plurality of patients, data for the patient and for all of the first plurality of patients coming from sources including Electronic Medical Records (EMR) and Electronic Health Records (EHR), Population Health/Analytic platforms, Care Management systems, and Case Management systems;

a care plan risk rating, each care plan risk rating indicating a patient's degree of compliance with that patient's care plan, and calculated according to that patient's responses to a predetermined series of questions regarding that patient's care plan;

storing, in the computer-implemented provider system, the responses and the care plan risk ratings;

wherein, for a given condition for which the first plurality of patients is being treated, and responsive to a determination that one or more of the care plan risk ratings justifies a change in one or more of the care plans for the first plurality of patients;

collecting, via the computer-implemented risk rating system, the care plan risk ratings for the plurality of patients;

instructing the change, via the computer-implemented risk rating system, responsive to the collective care plan risk ratings for the first plurality of patients; and communicating the change, via one of the computer-implemented provider system and the computer-implemented risk rating system, to those of the first plurality of patients whose care plan risk ratings justify the change;

assembling, via one of the computer-implemented provider system and the computer-implemented risk rating system, the care plan risk ratings for the first plurality of patients into a further plurality of patient cohorts, different from said first plurality of patient cohorts, according to predetermined criteria which comprise a predetermined threshold or a predetermined range for the assembled care plan risk ratings, wherein each of the further plurality of patient cohorts comprises care plan risk ratings for patients of a plurality of physicians;

wherein a first one of the further plurality of patient cohorts comprises care plan risk ratings above a first threshold; a second one of the further plurality of patient cohorts comprises care plan risk ratings between the first threshold and a second threshold; and a third one of the further plurality of patient cohorts comprises care plan risk ratings above the second threshold, wherein care plan risk ratings above said second threshold indicate substantial compliance with care plans; and wherein one of the provider system and the risk rating system may implement said change in one or more of the care plans for the first plurality of patients in the third one of the further plurality of patient cohorts, responsive to the patients not showing sufficient improvement despite having care plan risk ratings above the second threshold.

5. A method as claimed in claim 4, wherein each of the predetermined series of questions has a weight assigned to it such that a sum of the weights for all of the predetermined series of questions equals 100%.

6. A method as claimed in claim 4, wherein the care plans comprise a plurality of items selected from the group consisting of prescriptions, medications, nutritional supplements, diet, exercise, laboratory tests, medical procedures, and one or more therapies.

* * * * *